(12) United States Patent
Anson et al.

(10) Patent No.: US 6,432,134 B1
(45) Date of Patent: Aug. 13, 2002

(54) METHOD OF PRODUCING A SURGICAL IMPLANT

(75) Inventors: Anthony Walter Anson, Middlesex; Peter William Phillips, Evesham; John Reidy; Shakeel Qureshi, both of London, all of (GB)

(73) Assignee: Anson Medical Limited (GB)

(*) Notice: Subject to any disclaimer, the term of this patent is extended or adjusted under 35 U.S.C. 154(b) by 0 days.

(21) Appl. No.: 09/214,683

(22) PCT Filed: Jul. 15, 1997

(86) PCT No.: PCT/GB97/01899

§ 371 (c)(1),
(2), (4) Date: Aug. 16, 1999

(87) PCT Pub. No.: WO98/02100

PCT Pub. Date: Jan. 22, 1998

(30) Foreign Application Priority Data

Jul. 16, 1996 (GB) .............................................. 9614950

(51) Int. Cl.⁷ ................................................. A61F 2/06
(52) U.S. Cl. ...................... 623/1.19; 623/901; 140/71 C
(58) Field of Search ................................. 606/213, 108, 606/151; 623/1.15, 1.19, 901; 140/71 R, 89, 71 C

(56) References Cited

U.S. PATENT DOCUMENTS 4,957,501 A   9/1990  Lahille et al. ............... 606/200
5,192,301 A   3/1993  Kamiya et al. ............. 606/198

FOREIGN PATENT DOCUMENTS

| DE | 233 303 A | 2/1986 |
| DE | 43 39 265 A1 | 5/1995 |
| EP | 0 323 333 A | 7/1989 |
| WO | 9211823 | 7/1992 |
| WO | 95/25480 | 9/1995 |

Primary Examiner—Michael H. Thaler
(74) Attorney, Agent, or Firm—Cesari and McKenna, LLP

(57) ABSTRACT

A stent for occluding the human ductus arteriosus comprises a length of wire of shape memory effect or superelastic material which is expandable from a relatively straightened state for introduction into the patient to an occluding state wherein the wire defines an occluding anchor part and a spiral anchor part and a straight linking part connecting the two wherein the wire has a series of turns extending over the cross-sectional area of the occluding anchor part.

4 Claims, 5 Drawing Sheets

METHOD OF PRODUCING A SURGICAL IMPLANT

Figure 1:
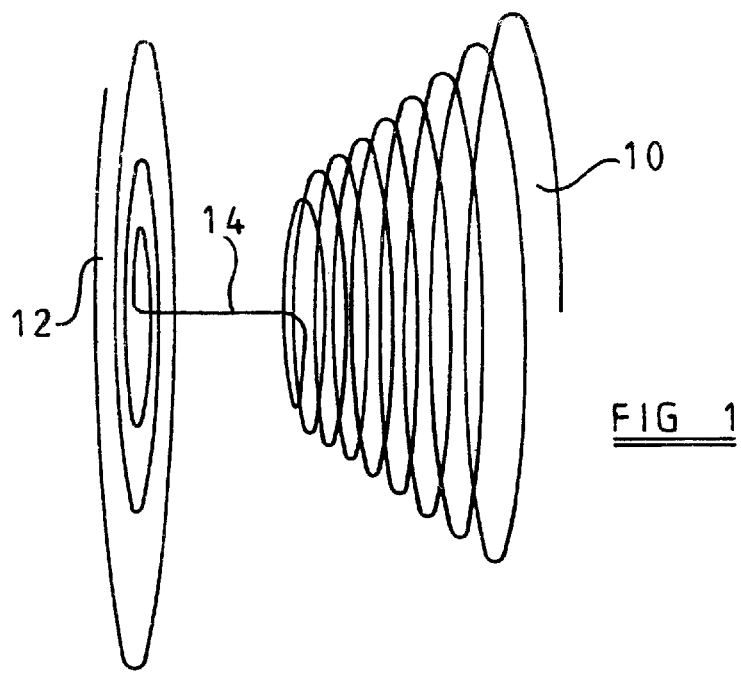

This invention relates to surgical implants which are commonly known as stents and more particularly to stents for occluding the human ductus arteriosus, cardiac septal defects and other blood vessels needing occlusion. This invention also relates to delivery systems for such stents and to methods of manufacturing such stents.

In the fetus, the ductus arteriosus is a patent vessel connecting the pulmonary artery to the aorta. At birth, a variety of physiological changes cause the ductus to constrict and it becomes permanently closed after one or two days. In a few cases, the ductus fails to occlude completely (patent ductus), allowing blood to flow from the aorta to the pulmonary artery, compromising respiration and circulation. Serious consequences may result.

Conversely, in some other circulatory birth defects in which the ductus has closed naturally, the patient benefits when the ductus is artificially re-opened.

Surgical interventions to alleviate a patent ductus arteriosus consist of either surgically ligating the leak path or implantation of a "single umbrella", such as the C R Bard PDA Umbrella. The delivery system for this device is large and it cannot be used in very small children. The clinical approaches currently in use are problematic; the surgery is major, requires significant exposure and has an associated morbidity. Technically, considerable difficulties can be experienced in accurately siting and deploying the umbrella device because of its large delivery system.

As an alternative to surgery, pharmacological agents can be used to constrict the ductus but this technique can only be used in babies and is not always successful. Also such agents have side effects.

There are many designs of stents currently in commercial use, the Gianturco, (EP0282175) Palmatz-Schatz, Wall stent and others are well known in the art. These stents are designed for use in vessels which are several times longer than their diameter and the stents share this aspect ratio. Most designs exhibit spring resistance to radial compression but nevertheless are intended to be approximately parallel sided cylindrical tubes, once implanted. The ductus arteriosus is short with respect to its diameter and as a result conventional stent designs are the wrong shape and tend to migrate. It is quite usual for surgeons to modify existing devices to make them more appropriate for implantation in this procedure. But this is not an ideal solution to the problem.

Existing stents are intended to maintain the patency of diseased blood vessels and to minimise the risk of creating further local disease or trauma. For instance, introduction of a stent can cause intimal hyperplasia by damaging plaques on the vessel wall. Blood flow which impinges on the stent may become turbulent and create further neo intimal proliferation. For these reasons, stents are usually designed with the minimum of material to reduce their surface area.

EP-A0666065 discloses stents for maintaining the patency of passages in the biliary, urinary or vascular system, wherein the stent is formed of a shape memory alloy (SMA) wire or mesh and can be changed thermally from a first configuration in which it has distal and proximal coiled or mesh cylindrical portions which are spaced apart, into a second configuration in which the proximal portion flares into a funnel shape which increases in diameter away from the distal portion which expands in diameter. However, such stents require a relatively large delivery system.

Other examples of stents based on SMA wire for maintaining the patency of vessels are disclosed in U.S. Pat. No. 3,868,956 and U.S. Pat. No. 4,512,338.

U.S. Pat. No. 5,192,301 and DD 233303 disclose a number of occluding stents for the ductus arteriosus based on SMA materials. However, none of these is capable of adopting a small cross-sectional area for delivery to the required site.

It is an object of a first aspect of the present invention to provide an occluding stent which is capable of being delivered and placed relatively easily.

According to said first aspect of the present invention, there is provided a stent for surgical implantation into a patient, said stent including a wire which is expandable from a relatively straightened state for introduction into the patient, to an occluding state wherein the wire defines an occluding anchor part in which the wire has adopted a series of turns extending over the cross-sectional area of the occluding anchor part.

The stent of the present invention, despite occupying a small cross-sectional area in its relatively straightened state, presents a significant surface area to blood flow in its expanded occluding state, both to increase the probability of clotting and to provide a significant support for mechanical, biological or pharmacological coatings or surface treatments. In one embodiment of the design, the stent can be used as a drug delivery vehicle by means of slow release pharmacological coatings. In another embodiment, the surface of the stent is roughened to provide an attractive substrate for cell adhesion so that the mechanical action of the device alone will fuse the ductus. Combinations of these characteristics are possible and the coatings or treatments can be applied over all or part of the surface of the stent.

Conveniently, in its expanded occluding state, the stent has three distinct regions which can be manufactured as separate components or as a monobloc construction and which comprise the occluding anchor part, another anchor part which may also have an occluding function, and a linking part between the anchor parts. The anchor parts are typically circular in section and their diameters are greater than the minimum diameter of the vessel within which the stent is placed. The stent may be placed such that the anchor parts are positioned either side of the narrowest part of the vessel. In this way it will be impossible for either anchor part to pass through the entire length of the vessel, preventing its migration. This construction is particularly suitable for short vessels which are to be occluded.

The link part may be a simple wire rod, or it may be a tube or mesh. Its principal function is to maintain the separation of the anchor parts to their designed value. It has an outer diameter which is less than the maximum outer diameters of either anchor part.

At least one of the anchor parts may be designed to lie within the vessel and have a conical form in the occluding state, expanding distally and applying a radially expansive force to secure it in position. Alternatively, at least one of the anchor parts is of substantially planar spiral form in its occluding state, and is sufficiently flexible that, upon expansion, it distorts so as to adopt the cross-sectional profile of the wall of the passage in which it is located in use.

If the stent is deployed close to the junction of the vessel with another, larger, vessel then one anchor part can have such a large diameter that it can only sit within the larger vessel. In this case, the form of the anchor part is conveniently planar or saddle shaped so that it conforms to the inner wall of the larger vessel.

The stent can be manufactured using established techniques such as helically wound wire, (single-stranded or twisted or braided multi-stranded) and welded wires, from metal or plastics including biodegradable plastics such as polylactic acid. Specifically included are shape memory effect materials, superelastic materials and polymers.

When a shape-memory effect material is employed, its transition temperature may be in the range of 0° C. to 50° C., permitting designs of stent which will trigger at blood temperature and therefore need to be actively cooled to keep them from deforming prematurely, or devices which trigger above blood temperature and so need to be actively heated to make them adopt their final shape. A number of means for heating can be employed, including perfusion with warm liquid, or electrical or induction heating.

The stent can be used on a wide range of ages of child from pre-term babies and neonates to infants and juniors. A range of appropriate sizes can be used which employ wire diameters from 0.2 mm to 0.9 mm, with the outer diameter of the anchor part 12 being in the range of 7 to 12 mm, the smaller diameter of the anchor part 10 being in the range of from 2 to 4 mm and the outer diameter being in the range of from 5 to 10 mm. The overall length of the stent will normally range from about 6 to 12 mm.

The stent may have its surfaces treated to facilitate both thrombus aggregation and natural cell proliferation. To induce these effects, the stent surface may be modified mechanically by abrasion or by attaching a protein, (eg thrombin or collagen) that initiates blood clotting and cell attachment. The materials and processes required for these coatings are well known per se in the art.

In some applications of the stent, the ends of the device will project into normal, healthy blood vessels whilst the central section of the stent lies in the section to be occluded. Coatings may be applied in zones onto the stent. In this way, the ends of the stent can be coated with thrombo-resistant materials whilst the central section can be coated with thrombus-promoting materials. Such coatings can be applied by a sequence of dipping and masking steps.

It is preferred to provide an insulating coating to mitigate possible problems of metal migration when certain dissimilar metals are in the presence of sodium, potassium and, particularly calcium ions. Examples of insulating coatings include the pyrolytic carbons known as "diamond-like carbon" (DLC) which have found application in the medical devices field as inert, corrosion-and abrasion-resistant materials. DLCs prevent migration of constituent metals from an alloy and prevent their entry into the body. In an additional embodiment, the stent types previously described are coated with a DLC film. Antithrombogenic or thrombogenic agents can be deposited on the DLC coating either directly or by means of an intermediate coating which enables an intimate attachment to both coating materials.

In cases where the stent is coated with agents to reduce thrombogenesis and atherogenesis, such agents may be held within a biodegradable matrix such as polylactic acid or polyglycolic acid which in themselves will control cell proliferation. This arrangement will yield a local, slow release of the active substances.

The stents according to the present invention are capable of being delivered down a very small catheter, allowing their use in smaller patients, and do not require open surgery. The stent does not require to be modified before use by the surgeon and has a sufficient surface area within the vessel lumen for pharmacological agents to be added which will augment the action of the stent in closing the ductus or other passageway to be occluded.

According to a second aspect of the present invention, there is provided a delivery system for placement of a stent according to said first aspect of the present invention in a patient, said system comprising (i) a catheter containing or adapted to contain said stent in its relatively straightened state, (ii) an elongate flexible placement member extending or being adapted to extend longitudinally of said catheter and having proximal and distal ends, and (iii) releasable connection means connecting or being adapted to connect the distal end of the placement member with the stent.

The catheter may be single or multiple lumen tube whose inner diameter allows the stent to pass through without hindrance. The catheter is preferably constructed of a material which resists permanent deformation after following a tortuous pathway through the vascular system. Many polymeric materials can be employed, of which polyvinyl chloride compounds and derivatives, polyurethanes and polyesters are typical of materials that can be employed.

The placement member may comprise a pusher wire used to push the stent through the catheter and deliver it to its final location. The wire will be an appropriate gauge to fit within the catheter without kinking. It may be linked to the stent via the connection means to allow the stent to be withdrawn if required.

In versions of the stent manufactured from thermal shape memory effect materials, the catheter is designed to insulate the stent from the ambient-blood heat and, optionally, to circulate cooling fluid around the catheter. If the stent is designed to trigger above blood temperature, the catheter may be used to deliver a bolus of warm fluid to trigger the stent once in place.

A shape memory effect material may also be used for the connection means or as a connector for many other uses. Thus, in accordance with a third aspect of the present invention, there is provided a releasable connector for releasably interconnecting first and second parts, said connector comprising first and second connector regions adapted to be secured respectively to the first and second parts, wherein the first connector region has a shape memory effect and is changeable from a first state to a second state above a predetermined trigger temperature, said first state being one in which the first connector region is adapted to hold the first part, and the second state being one in which the first connector region is adapted to release the first part so as to enable the first and second parts to be disconnected.

According to a fourth aspect of the present invention, there is provided a method of producing a shaped article, eg a stent such as a stent according to said first aspect of the present invention, comprising the steps of (a) winding a length of shape memory material onto a mandrel to form a series of turns defining a coil region having a longitudinal extent; (b) treating the material wound onto the mandrel so as to set therein a memory of the shape of the coil region; (c) removing the wound material from the mandrel; (d) treating the removed material so as to recover the memorised shape of the coil region; (e) changing the length of the coil region; and (f) treating the material so as to set therein a memory of the changed shape of the coil region.

Step (e) is effected by reducing the length of the coil region, possibly so that it is substantially planar. The coil region resulting from step (b) may be of circular or non-circular cross-section and may have a cross-section which tapers longitudinally of the coil region.

Between steps (d) and (f), one or more of the turns defining the coil region may displaced laterally of the direction of longitudinal extent of the coil region.

Figure 2:
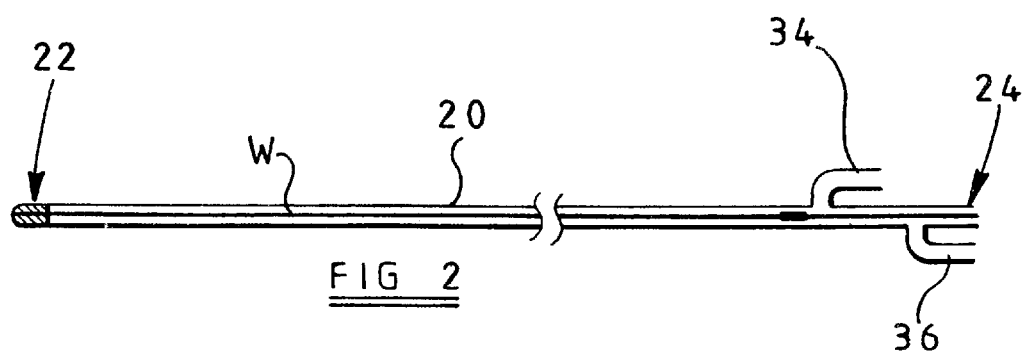
Figure 3:
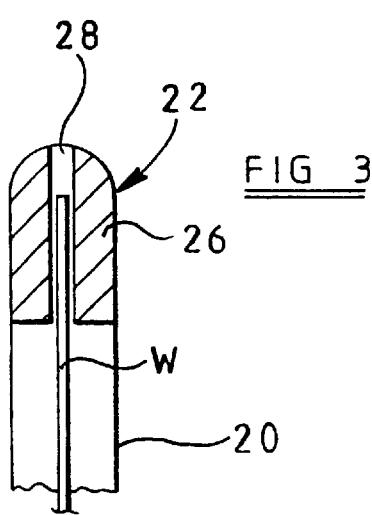
Figure 4:
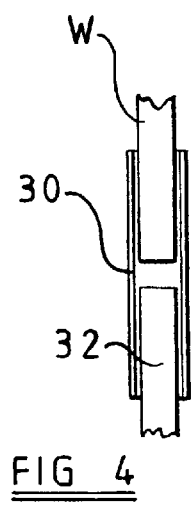
Figure 5:
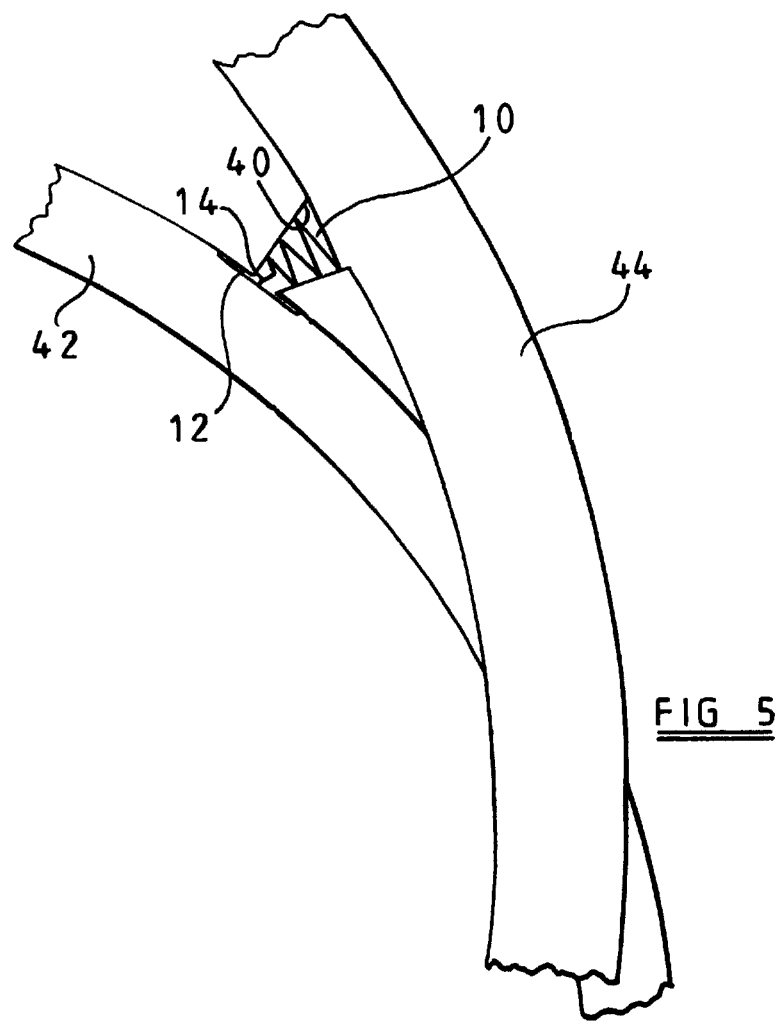
Figure 6:
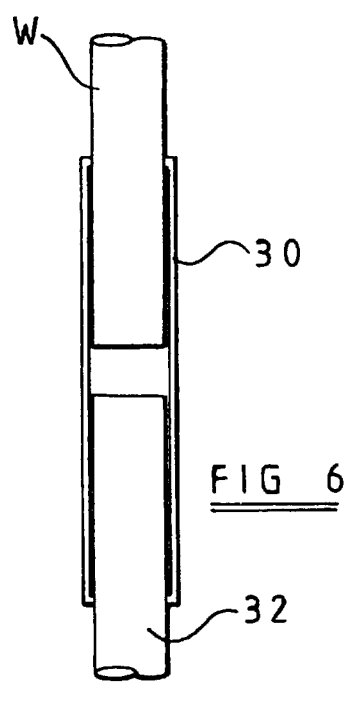
Figure 7:
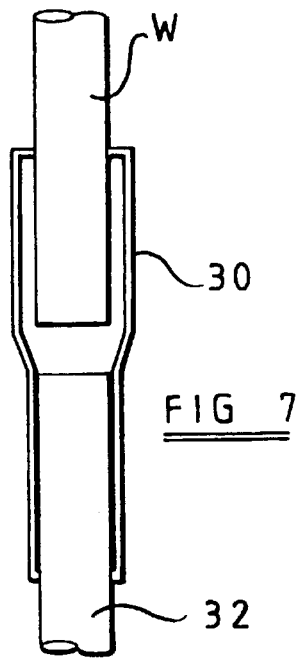
Figure 8:
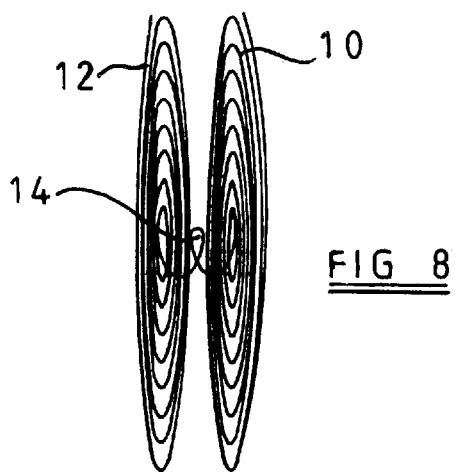
Figure 9:
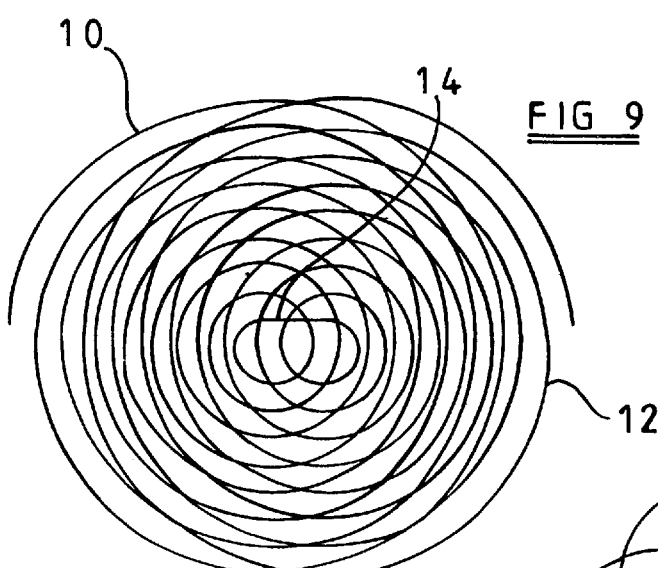
Figure 10:
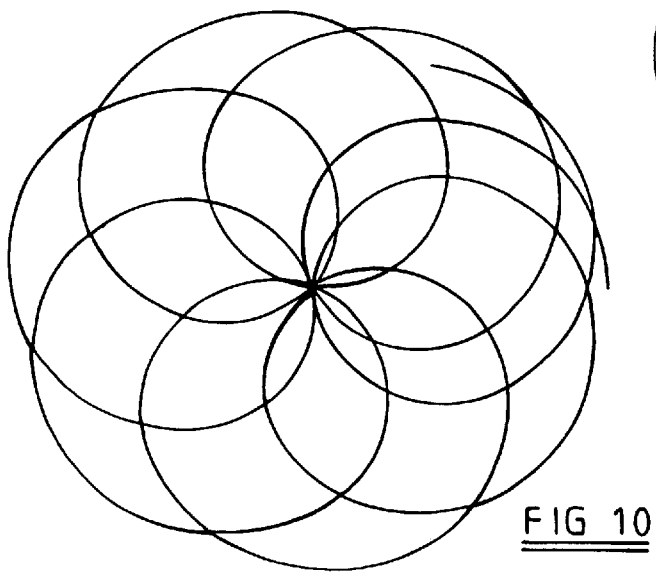
Figure 11:
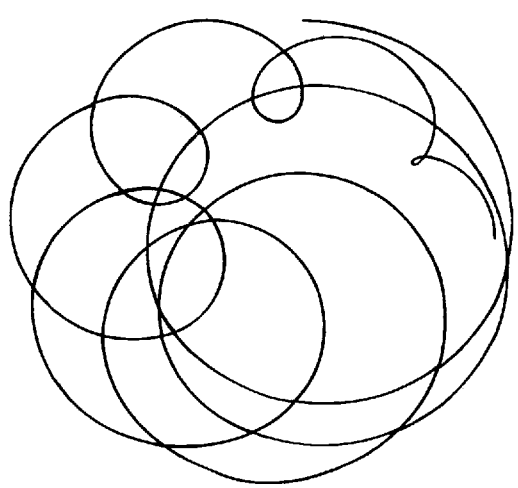
Figure 12A:
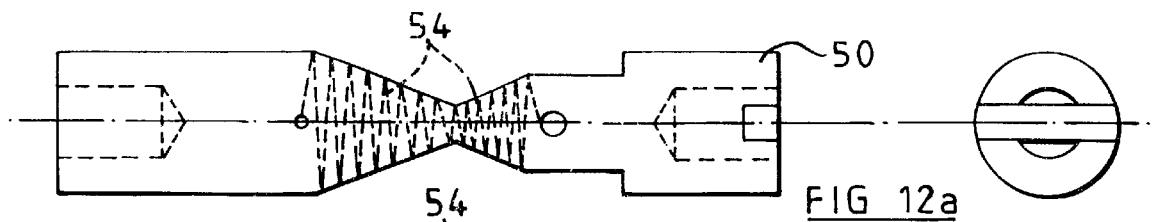
Figure 12B:
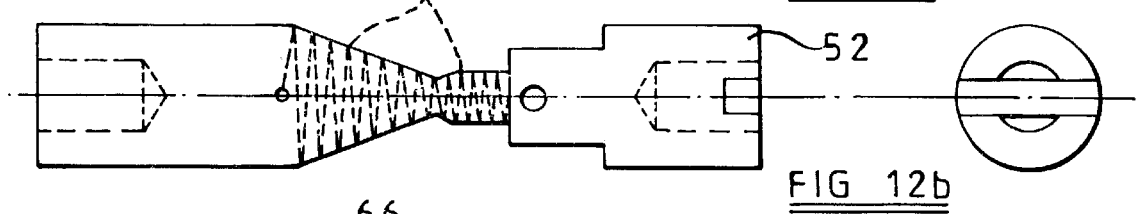
Figure 13A:
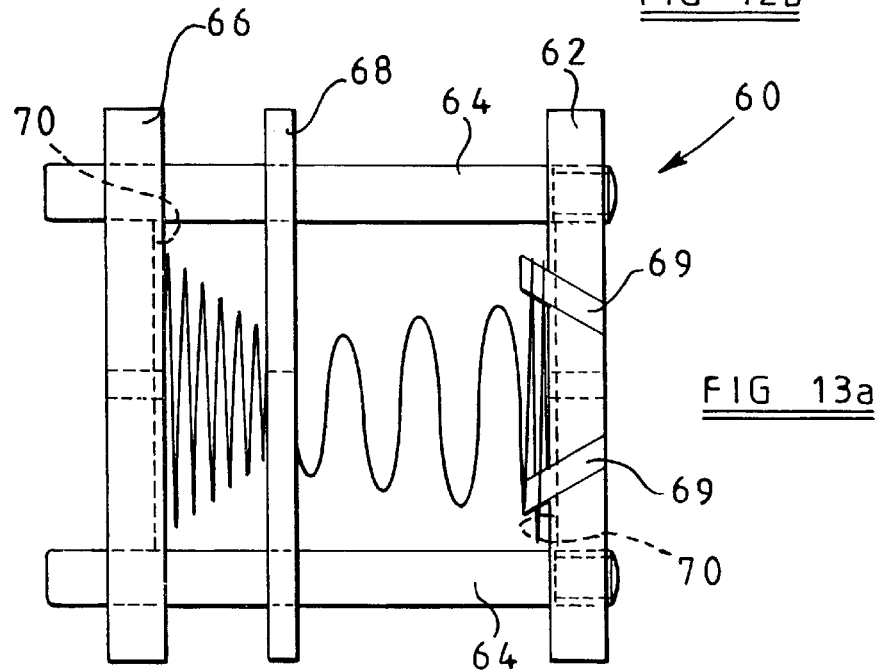
Figure 13B:
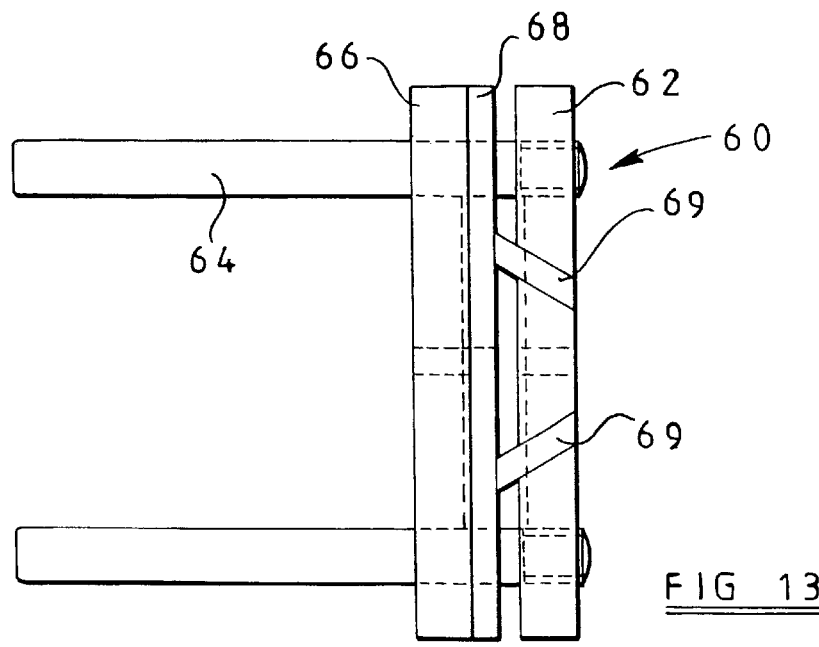
Figure 14:
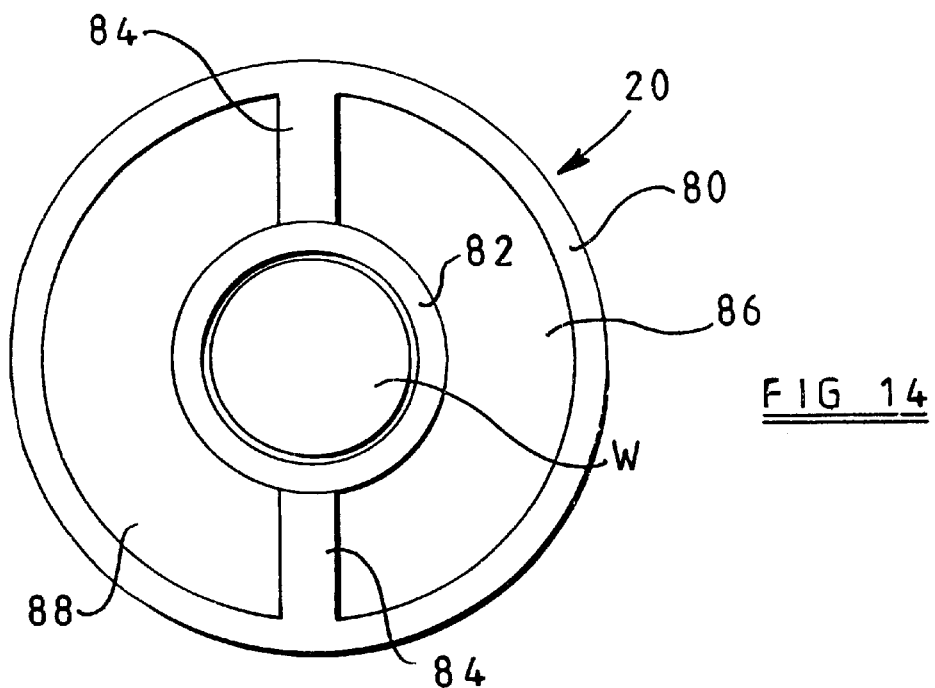
Figure 15:
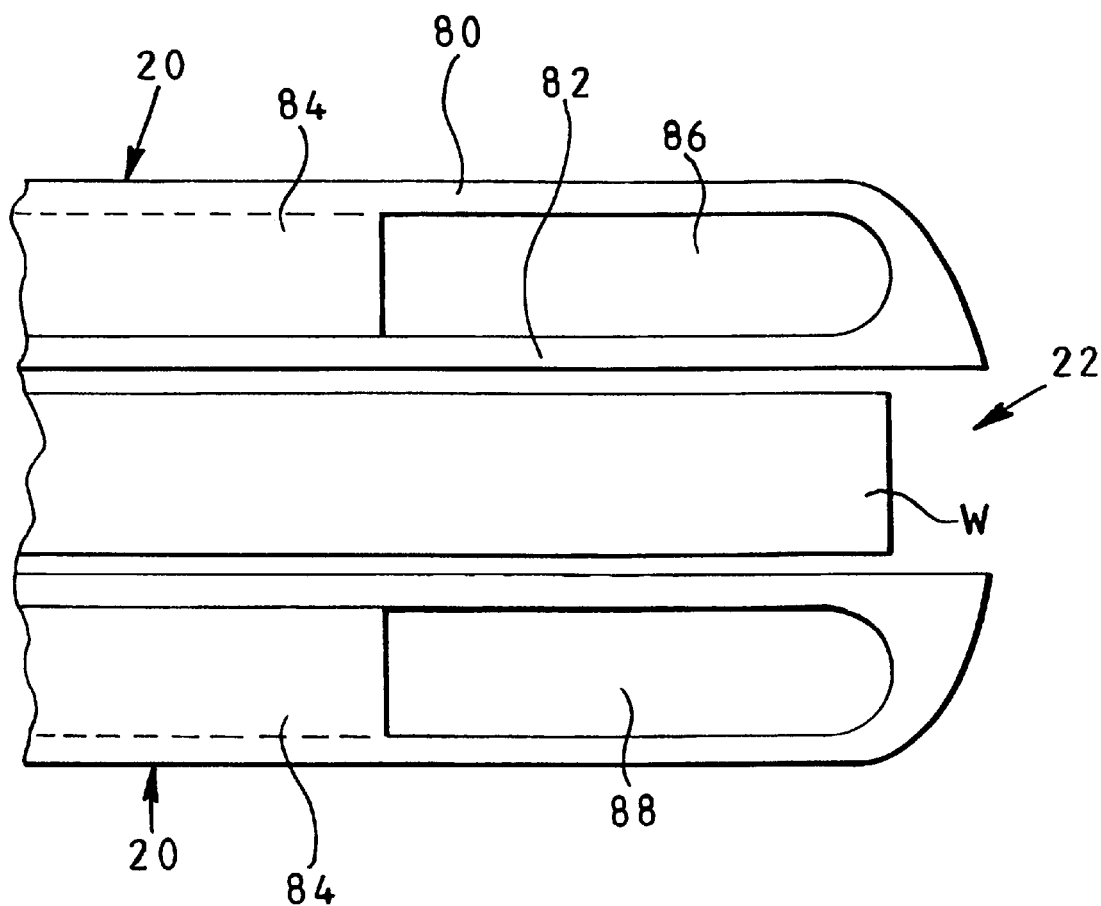

Embodiments of the present invention will now be described, by way of example, with reference to the accompanying drawings, in which:

FIG. 1 is a schematic perspective view of a first embodiment of stent according to the present invention shown in an expanded, occluding state, FIG. 2 is a schematic view of a delivery system for placement of the stent of FIG. 1, showing the stent in a relatively straightened state, FIG. 3 is a section of a distal end of the system of FIG. 2, FIG. 4 is a section showing a connector forming part of the delivery system of FIG. 2, FIG. 5 is a schematic view showing the stent of FIG. 1 positioned so as to occlude the human ductus arteriosus, FIGS. 6 and 7 are schematic axial sections through an embodiment of releasable connector according to said third aspect of the present invention, FIG. 8 is a perspective view of a second embodiment of stent according to the present invention, FIGS. 9 to 11 are schematic views showing alternative forms of occluding region of a stent according to the present invention, FIGS. 12a and 12b are side views of double conical and conical-cylindrical mandrels for forming stents according to the present invention, FIGS. 13a and 13b are schematic views of a flattening clamp used in the formation of a stent, FIG. 14 is a cross-sectional view of a catheter for delivering a stent according to the present invention, and FIG. 15 is an axial section through the catheter of FIG. 14.

Referring now to FIG. 1 of the drawings, the stent illustrated therein is for occluding the ductus arteriosus and is formed of a wire of shape memory effect material, preferably the near equi-atomic nickel and titanium alloy which is known per se. In an expanded, occluding state, the stent comprises an occluding anchor portion 10 formed by a series of turns of the wire so that a conical helix form is defined. The stent further comprises another anchor portion 12 formed, by a scroll or spirally wound part of the wire. The anchor parts 10 and 12 are interconnected by a straight linking part 14 extending axially of the cone defined by the occluding anchor part 10 and perpendicularly with respect to the plane of the spiral anchor part 12. As can be seen from FIG. 1, a single length of wire forms the whole device.

When the shape memory effect alloy is in a martensitic condition, the stent is malleable and can be deformed into a straight wire W (see FIG. 2). Typically, the wire has a diameter of 0.3 mm and is arranged to convert from martensite to austenite at or slightly above 37° C. Such conversion causes the substantially straight length of wire W as illustrated in FIG. 2 to convert to the shape illustrated in FIG. 1 after release by the delivery system at the desired placement site, as will be described hereinafter.

Referring now to FIGS. 2 to 4, the delivery system illustrated therein comprises a catheter 20 having a distal end 22 and a proximal end 24. At its distal end 22, the catheter 20 is closed by a compliant elastomer guide/seal member 26 having a spherically rounded end with a central bore 28 therethrough receiving a distal end of the wire W. A proximal end of the wire W is a friction fit within a stainless steel connector bush (see particularly FIG. 4) within the catheter 20. The connector bush 30 also receives a stainless steel pusher wire 32 extending out of the proximal end 24 of the catheter 20. The catheter 20 is provided with cooling liquid inlet and outlet ports 34 and 36, respectively.

In use, with the wire W of the stent straightened and contained in the catheter 20, the distal end 22 of the catheter is introduced into the vascular system via a suitable point, such as the femoral artery, and the stent is positioned within the ductus 40 (see FIG. 5) which interconnects the pulmonary artery 42 and the aorta 44 and which is required to be occluded. Until being delivered to the ductus 40, the wire W is maintained in its martensitic form by circulating coolant through the catheter 20 via the ports 34 and 36. Ejection of the stent from the catheter 20 is effected by holding the catheter 20 steady whilst pushing on the wire to cause the wire W to be ejected through the member 26 at the distal end 22. As the stent is ejected, it is warmed by blood at 37° C., causing the stent to expand so as adopt the structure illustrated in FIGS. 1 and 5.

Disengagement of the wire 32 from the stent is effected simply by pulling on the wire 32 so that the bush 30 slides off the wire W which is now firmly anchored in the ductus 40, the strength of the friction fit between the wire W and the bush 30 being sufficient to permit this to take place. The strength of the friction fit is such that it can exert a force on the stent which is greater than that required to withdraw a partially deployed stent but less than that required to withdraw a fully deployed stent. In this way, the stent can be controlled and repositioned as well as being finally ejected.

Referring now to FIGS. 6 and 7, an alternative arrangement of bush 30 is formed of shape memory alloy material instead of stainless steel. In this case, the arrangement is such that, upon heating, that portion of the bush 30 which engages the wire W expands into its memorised condition, thereby releasing the wire W. The bush 32 is deformed in its low temperature condition by radially compressing or crimping it around the wire W so that it is held firmly. By careful design of these parts, the stent can still recovered even when 95% of it has been ejected.

The portion of the bush 30 which is engaged with the wire 32 does not have a memory of increased diameter and therefore remains securely attached to the latter. The wire 32 can be made from a number of metals that have kink resistance and suitable spring qualities.

In a further embodiment (not shown), the stent is held in the end of a long plastics tube by an interference fit. A wire which is a sliding fit within the plastics tube is used to stiffen the tube and to eject the stent from the end of the plastics tube.

In a further modification (also not shown), at least the tip of the catheter at the distal end thereof has a second lumen which allows it to be slipped over and to follow a previously-introduced guide wire. Such a technique is per se known in the art.

Referring now to FIGS. 8 and 9 of the drawings, the stent illustrated therein consists of a wire formed of two spirally wound anchor parts 10 and 12 interconnected by link part 14 formed of a loop of the length of wire forming the anchor parts 10 and 12. As can be seen from FIG. 9, the spiral windings of the anchor parts 10 and 12 are wound in the opposite sense and have their central axes slightly laterally displaced. In this way, there is an enhanced occluding effect. The wire is a thin shape-memory alloy wire where the resilience properties of the spiral coils forming the anchor parts 10 and 12 made from thinner wires means that they will conform to the shape of the vessel in which they are implanted and project as little as possible beyond the vessel. As can be seen from FIGS. 8 and 9, the anchor parts 10 and 12 are planar and the link part 14 is a part turn or loop. Alternately, it may be a whole turn or several turns of wire which join the centres of the spiral anchor parts 10 and 12. The length of the link part 14 between the anchor parts 10 and 12 will generally be between 0.1 and 5 mm. Instead of being spiral, one or more of the anchor parts 10 and 12 may be cycloidal (FIG. 10) or spiral-cycloidal (FIG. 11).

When implanted, the planar anchor portions 10 and 12 will be distorted by the walls of the vessels in which the are implanted, yielding an implant which has either two conical anchor portions, two flat anchor portions, or one flat and one conical anchor portion. In all cases, the implant will have been stretched longitudinally and its elastic recoil will ensure that the implant has adopted the minimum length possible within the anatomy and that it therefore projects as little as possible into the vessels on either side of the implant.

The typical dimensions of the implant are:

| | |
|---|---|
| Maximum diameter of first helix | 2 mm |
| Minimum diameter of first helix | 2 mm |
| Number of turns, first helix | 10 turns |
| Maximum diameter of second helix | 12 mm |
| Minimum diameter of second helix | 2 mm |
| Number of turns, second helix | 10 turns |
| Length of connecting part | 1 mm |
| Wire diameter | 0.2 mm |

The above typical dimensions may be varied by at least ±50% depending upon the extent of biological variation of patients to be fitted with the stent implant.

In some cases, it may be desirable for the minimum diameter of one or both of the spiral anchor parts 10 and 12 to be less than 2 mm, although this figure is limited by the diameter of the wire employed. Generally, nickel-titanium shape memory alloy wire cannot be completely straightened when it has been formed into a coil of a diameter less than 10 times the diameter of the constituent wire. This limitation may be overcome by constructing the stent implant from thin wire chosen to be approximately one tenth the diameter of the minimum diameter of the spiral anchor part 10 or 12. This results in a simple implant of reduced mechanical strength.

Alternatively, a multi-stranded wire may be employed made from a number of finer wires twisted or braided together to form the stent implant. This results in a more complex implant of greater mechanical strength.

The manufacture of wire spirals is very common using mandrel-based winding techniques or centreless, roller-based forming processes. However, the manufacture of paired spirals interconnected at their centres and nominally flat or asymmetric forms is more complex. A three-stage procedure for achieving these latter forms when manufactured from shape memory alloy will now be described with reference to FIGS. 12a and 12b and 13a and 13b. This procedure involves winding the shape-memory alloy wire onto a double frusto-conical mandrel 50 (FIG. 12a) or a conical cylindrical-mandrel 52 (FIG. 12b). In each case, the wire is wound into a deep groove thread 54 of the appropriate shape cut into the periphery of the mandrel 50 or 52. Normally, this shape would be impossible to remove from the mandrel. However, although the wire shape may be destroyed when removing it from the mandrel, the form can be recovered when the material is warmed above, its trigger temperature. The shape of the mandrel 50 or 52 defines the number of wire turns in the stent and the diameters of those turns. Once wound onto the mandrel 50 or 52, the wire is fixed at its ends by appropriate clamps or attachment means (not shown). Then, the entire assembly of wire and mandrel is heat-treated so that the wire will adopt the shape imparted by the mandrel when its memory is recovered. This temperature is usually in the region of 350° C. to 550° C.

After cooling, the wire is removed from the mandrel 50 or 52 and heated gently to make it re-adopt the shape of the mandrel, typically a long spiral whose diameter varies along its length. This is then inserted into a flattening clamp assembly 60 (see FIGS. 13a and 13b). The flattening clamp 60 includes a fixed clamp member 62 from which guide rods 64 extend. A movable clamp member 66 and a divider 68 are slidably mounted on the rods 64 and slidable on the rods 64 from an unclamped position as illustrated in FIG. 13a to a clamped position as illustrated in FIG. 13b. The clamp member 62 carries a series of hooks or pegs 69 which are used to trap and retain one or more turns of the spiral in a position which is laterally offset from the axis of the spiral. When six or seven hooks or pegs 69 used to trap individual coils of a parallel-sided cylindrical spiral, the cycloidal pattern illustrated in FIG. 10 can be produced. Similarly, a conically-sided spiral used with the same number of hooks or pegs 69 can produce the less-symmetrical spiral-cycloidal pattern illustrated in FIG. 11. If only one hook or peg 69 is used, the entire axis of the trapped spiral can be offset from the untrapped part, resulting in the pattern illustrated in FIG. 9. Such hooks or pegs 69 may be provided on the clamp member 62 or on the divider 68.

Pockets 70 are provided in both clamp members 62 and 66. These define the overall length of the sections of the spiral contained within them. Alternatively or additionally, one or more of the pockets 70 may be provided in the appropriate surface or surfaces of the divider 68. In a further embodiment, the divider 68 may be omitted completely, or more than one divider 68 may be provided. When no dividers 68 are used, a flat spiral of zero longitudinal pitch is produced. The divider or dividers can be introduced to define the longitudinal pitch of particular turns of the spiral.

When the appropriate divider(s) 68 and hook(s) or peg(s) 69 have been fitted to impose the required secondary structure to the spiral, the various parts are compressed together as illustrated in FIG. 13b and locked in place, followed by further heat treatment. Such further heat treatment is carried out in two steps, namely annealing at high temperature to remove all "memory" of the shape retained from the mandrel, and treatment at a lower temperature to "memorise" the shape in which the wire is held in the flattening clamp. The final shape of the stent is produced when it has been released from the flattening clamp.

Referring now to FIGS. 14 and 15, the catheter illustrated therein comprises outer and inner walls 80 and 82 which are maintained in spaced apart relationship by a pair of internal ribs 84 which divide the area between the walls 80 and 82 longitudinally into feed and return passages 86 and 88 for cooling liquid. These ribs are removed at the distal end 22 of the catheter 20 so as to allow the liquid from the feed passage 86 to return via the passage 88.

What is claimed is:

1. A method of producing a shaped article, comprising the steps of (a) winding a length of shape memory material onto a mandrel to form a series of turns defining a coil region having a longitudinal extent; (b) treating the material wound onto the mandrel so as to set therein a memory of the shape of the coil region; (c) removing the wound material from the mandrel; (d) treating the removed material so as to recover the memorised shape of the coil region; (e) changing the length of the coil region; and (f) treating the material so as to set therein a memory of the changed shape of the coil region.

2. A method as claimed in claim 1, wherein step (e) is effected by reducing the length of the coil region.

3. A method as claimed in claim 1, wherein the coil region is reduced in length so that it is substantially planar.

4. A method as claimed in claim 1, wherein between steps (d) and (f), one or more of the turns defining the coil region are displaced laterally of the direction of longitudinal extent of the coil region.

* * * * *